(12) United States Patent
Swanson et al.

(10) Patent No.: US 6,261,237 B1
(45) Date of Patent: Jul. 17, 2001

(54) THIN FILM PIEZOELECTRIC POLYMER SENSOR

(75) Inventors: Cal T. Swanson, Apex; Simon J. Lewandowski; Charles E. Chassaing, both of Raleigh; Michael Z. Sleva, Charlotte, all of NC (US)

(73) Assignee: MedAcoustics, Inc., Raleigh, NC (US)

( * ) Notice: Subject to any disclaimer, the term of this patent is extended or adjusted under 35 U.S.C. 154(b) by 0 days.

(21) Appl. No.: 09/136,933

(22) Filed: Aug. 20, 1998

(51) Int. Cl.[7] .......................................................... A61B 7/04
(52) U.S. Cl. ............................................. 600/527; 600/528
(58) Field of Search ................................... 600/527, 528, 600/595

(56) References Cited

U.S. PATENT DOCUMENTS

| | | |
|---|---|---|
| 32,180 | 4/1861 | Chase . |
| 3,442,264 | 5/1969 | Levitt . |
| 3,573,394 | * 4/1971 | Birnbaum ............................. 600/528 |

(List continued on next page.)

FOREIGN PATENT DOCUMENTS

| | | |
|---|---|---|
| 2703781A | 8/1978 | (DE) . |
| 3234584A1 | 3/1984 | (DE) . |
| 3531399A1 | 3/1986 | (DE) . |
| 19649679A | 8/1997 | (DE) . |
| 0194823A2 | 9/1986 | (EP) . |
| 0201421A1 | 11/1986 | (EP) . |
| 0325805A2 | 8/1989 | (EP) . |
| 0528279A1 | 2/1993 | (EP) . |
| 2507424 | 12/1982 | (FR) . |
| 2166871A | 5/1986 | (GB) . |
| 2188732 | 10/1987 | (GB) . |
| 04126135 | 4/1992 | (JP) . |
| WO/90-08506 | 8/1990 | (WO) . |
| WO92/08407 | 5/1992 | (WO) . |
| WO 93/22970 | 11/1993 | (WO) . |
| WOA9405207 | 3/1994 | (WO) . |
| WO 95/06525 | 3/1995 | (WO) . |

OTHER PUBLICATIONS

Akay et al., "Application of Adaptive FTF/FAEST Zero Tracking Filters to Noninvasive Characterization of the Sound Pattern Caused by Coronary Artery Stenosis Before and After Angioplasty," Annals of Biomedical Engineering, vol. 21, pp. 9–17 (1993).

(List continued on next page.)

Primary Examiner—George R. Evanisko
(74) Attorney, Agent, or Firm—Myers Bigel Sibley & Sajovec, P.A.

(57) ABSTRACT

A thin film piezoelectric polymer acoustic sensor for the passive detection of heart and blood flow sounds is described. Sensors may have initially slack film components which are tented by the mass of a housing when a sensor is positioned on acoustic medium. Enhanced sensor performance is provided by accommodation of the sensor spring constant to the spring constant of human flesh. Sensor performance may be enhanced by a combination of physical parameter ranges. A plurality of sensors may compose a linear array or an array aperture.

33 Claims, 10 Drawing Sheets

U.S. PATENT DOCUMENTS

| | | |
|---|---|---|
| 3,799,147 | 3/1974 | Adolph et al. . |
| 3,903,733 | 9/1975 | Murayama et al. . |
| 4,008,408 | 2/1977 | Kodama ................................ 310/9.1 |
| 4,054,808 | 10/1977 | Tanaka . |
| 4,094,308 | 6/1978 | Cormier . |
| 4,146,955 | 4/1979 | Young, Jr. et al. . |
| 4,226,248 | 10/1980 | Manoli . |
| 4,234,813 | 11/1980 | Iguchi et al. . |
| 4,255,791 | 3/1981 | Martin . |
| 4,268,912 | 5/1981 | Congdon . |
| 4,308,870 | 1/1982 | Arkans . |
| 4,376,302 | 3/1983 | Miller . |
| 4,385,255 | 5/1983 | Yamaguchi et al. . |
| 4,387,378 | 6/1983 | Henderson . |
| 4,406,967 | 9/1983 | Obara et al. . |
| 4,413,630 | 11/1983 | Anderson et al. . |
| 4,424,465 | 1/1984 | Ohigashi et al. . |
| 4,428,380 | 1/1984 | Wong et al. . |
| 4,458,693 | 7/1984 | Badzinski et al. . |
| 4,491,051 | 1/1985 | Barcus . |
| 4,509,527 | 4/1985 | Fraden . |
| 4,546,777 | 10/1985 | Groch et al. . |
| 4,549,551 | 10/1985 | Dyck et al. . |
| 4,586,514 | 5/1986 | Schlager et al. . |
| 4,628,321 | 12/1986 | Martin . |
| 4,630,203 | 12/1986 | Szirtes . |
| 4,656,385 | 4/1987 | Tanaka . |
| 4,697,597 | 10/1987 | Sanz et al. . |
| 4,700,712 | 10/1987 | Schmid . |
| 4,712,565 | 12/1987 | Katz et al. . |
| 4,742,458 | 5/1988 | Nathans et al. . |
| 4,777,961 | 10/1988 | Saltzman . |
| 4,781,200 | 11/1988 | Baker . |
| 4,784,154 | 11/1988 | Shirley et al. . |
| 4,792,145 | 12/1988 | Eisenberg et al. . |
| 4,803,986 | 2/1989 | Dufresne et al. . |
| 4,803,996 | 2/1989 | Peel et al. . |
| 4,805,633 | 2/1989 | Kotani et al. . |
| 4,812,976 | 3/1989 | Lundy . |
| 4,821,584 | 4/1989 | Lembke . |
| 4,840,183 | 6/1989 | Takahashi et al. . |
| 4,842,411 | 6/1989 | Wood . |
| 4,862,144 | 8/1989 | Tao . |
| 4,862,361 | 8/1989 | Gordon et al. . |
| 4,862,897 | 9/1989 | Eisenberg et al. . |
| 4,905,706 | 3/1990 | Duff et al. . |
| 4,924,875 | 5/1990 | Chamoun . |
| 4,928,705 | 5/1990 | Sekhar et al. . |
| 4,947,859 | 8/1990 | Brewer et al. . |
| 4,957,369 | 9/1990 | Antonsson . |
| 4,967,760 | 11/1990 | Bennett, Jr. et al. . |
| 4,991,581 | 2/1991 | Andries . |
| 5,002,058 | 3/1991 | Martinelli . |
| 5,002,060 | 3/1991 | Nedivi . |
| 5,003,605 | 3/1991 | Phillips et al. . |
| 5,010,889 | 4/1991 | Bredesen et al. . |
| 5,012,815 | 5/1991 | Bennett, Jr. et al. . |
| 5,025,809 | 6/1991 | Johnson et al. . |
| 5,035,247 | 7/1991 | Heimann . |
| 5,036,857 | 8/1991 | Semmlow et al. . |
| 5,056,201 | 10/1991 | Kasuga et al. . |
| 5,086,776 | 2/1992 | Fowler, Jr. et al. . |
| 5,109,863 | 5/1992 | Semmlow et al. . |
| 5,129,403 | 7/1992 | Henriquez et al. . |
| 5,140,992 | 8/1992 | Zuckerwar et al. . |
| 5,164,627 | 11/1992 | Popek . |
| 5,176,153 | 1/1993 | Eberhardt . |
| 5,213,108 | 5/1993 | Bredesen et al. . |
| 5,218,969 | 6/1993 | Bredesen et al. . |
| 5,301,679 | 4/1994 | Taylor . |
| 5,315,512 | 5/1994 | Roth . |
| 5,337,752 | 8/1994 | Reeves . |
| 5,363,401 | 11/1994 | Lucas et al. . |
| 5,365,937 | * 11/1994 | Reeves et al. ..................... 600/528 |
| 5,381,804 | 1/1995 | Shambroom . |
| 5,406,952 | * 4/1995 | Barnes et al. ..................... 600/500 |
| 5,455,385 | 10/1995 | Newton et al. . |
| 5,501,229 | 3/1996 | Selker et al. . |
| 5,551,437 | 9/1996 | Llöetscher ........................ 128/672 |
| 5,553,113 | 9/1996 | Weedon . |
| 5,595,188 | 1/1997 | Kassal . |
| 5,598,845 | 2/1997 | Chandraratna et al. . |
| 5,617,869 | 4/1997 | Austin et al. . |
| 5,638,823 | 6/1997 | Akay et al. . |
| 5,673,702 | 10/1997 | Albrecht et al. . |
| 5,680,513 | 10/1997 | Hyland et al. . |
| 5,686,917 | 11/1997 | Odom et al. . |
| 5,687,738 | 11/1997 | Shapiro et al. . |
| 5,704,365 | 1/1998 | Albrecht et al. . |
| 5,718,233 | 2/1998 | Selker et al. . |
| 5,724,967 | 3/1998 | Venkatachalam . |
| 5,724,968 | 3/1998 | Iliff . |
| 5,724,983 | 3/1998 | Selker et al. . |
| 5,796,920 | 8/1998 | Hyland . |
| 5,807,268 | 9/1998 | Reeves et al. . |

OTHER PUBLICATIONS

Akay et al., "Application of Adaptive Filters to Noninvasive Acoustical Detection of Coronary Occlusions Before and After Angioplasty," IEEE Transactions on Biomedical Engineering, vol. 39, No. 2, pp. 176–183 (Feb. 1992).

Akay et al., "Noninvasive acoustical detection of coronary artery disease using the adaptive line enhancer method," Medical & Biological Engineering & Computing, vol. 30, pp. 147–154 (Mar. 1992).

Akay et al., "Noninvasive Acoustical Detection of Coronary Artery Disease: A Comparative Study of Signal Processing Methods," IEEE Transactions on Biomedical Engineering, vol. 40, No. 6, pp. 571–5784 (Jun. 1993).

Donnerstein, "Continuous Spectral Analysis of Heart Murmurs for Evaluating Stenotic Cardiac Lesions," The Am. Journ. Card., vol. 64, pp. 625–630 (Sep. 15, 1989).

Durand et al., "Evaluation of FFT–Based and Modern Parametric Methods for the Spectral Analysis of Bioprosthetic Valve Sounds," IEEE Trans. on Biomedical Eng., vol. BME–33, No. 6, pp. 572–578 (Jun. 1986).

Foale et al., "Detection of aortic porcine valve dysfunction by maximum entrophy spectral analysis," Circulation, vol. 68, No. 1, pp. 42–49 (Jul. 1983).

Fraden, "Application of Piezo/Pyroelectric Films in Medical Transducers," Jour. of Clinical Eng., vol. 13, No. 3, pp. 133–138 (Mar.–Apr. 1988).

Iwata et al., "Algorithm for Detecting the First and Second Heart Sounds by Spectral Tracking," Medical & Biological Engineering and Computing, pp. 19–26 (Jan. 1980).

Johnson et al., "Estimation of the Severity of Aortic Valve Stenosis by Frequency Analysis of the Murmur," J. Am. Coll. Cardiol., 1(5):1315–23 (1983).

Johnson et al., "Evaluation of Aortic Stenosis by Spectral Analysis of the Murmur," JACC, vol. 6, No. 1, pp. 55–65 (Jul. 1985).

Joo et al."Pole–Zero Modeling and Classification of Phonocardiograms," IEEE Trans. on Biomedical Eng., vol. BME–30, No. 2, pp. 110–118 (Feb. 1983).

Kagawa et al., "Real–time sound spectroanalysis for diagnosis of malfunctioning prosthetic valves," J. Thorac. Cardiovasc. Surg., vol. 79, pp. 671–679 (May 1980).

Lees et al., "Phonoangiography: A New Noninvasive Diagnostic Method for Studying Arterial Disease," Proceedings of the National Academy of Sciences, vol. 67, No. 2, pp. 935–942 (Oct. 1970).

Qian et al., "Orthogonal–Like Discrete Gabor Expansion," 26th Conf. on Infor. Sci an Systems, Princeton University (Mar. 18, 1992).

Semmlow et al., Noninvasive Detection of Coronary Artery Disease Using Parametric Spectral Analysis Methods, *IEEE Engineering in Medicine and Biology Magazine*, pp. 33–36 (Mar. 1990).

Semmlow et al., "Coronary Artery Disease—Correlates Between Diastolic Auditory Characteristics and Coronary Artery Stenoses," *IEEE Transactions on Biomedical Engineering*, vol. BME–30, No. 2, pp. 136–139 (Feb. 1983).

Semmlow et al., "Non–Invasive Diagnosis of Coronary Artery Disease by Enhanced Coronary Phonocardiography," IEEE Frontiers of Eng. in Health Care, pp. 181–185 (1982).

Stein et al., "Frequency Spectra of the First Heart Sound and of the Aortic Component of the Second Heart Sound in Patients with Degenerated Porcine Bioprosthetic Valves," The Am. Journ. of Carad., vol. 53, pp. 557–581 (Feb. 1, 1984).

von Gierke, H. et al., "Physics of Vibrations in Living Tissues," J. App. Physiology, vol. 4, pp. 886–900 (Jun. 1952).

Wang et al., Modeling Sound Generation in Stenosed Coronary Arteries, IEEE Transactions on Biomedical Engineering, vol. 37, No. 11, pp. 1087–1094 (Nov. 1990).

PCT International Search Report, PCT International Application No. PCT/US99/18459, mailed Jan. 12, 1999).

* cited by examiner

THIN FILM PIEZOELECTRIC POLYMER SENSOR

FIELD OF THE INVENTION

This invention relates to a flexible, thin-film sensor for the passive acoustic detection of heart and blood-flow sounds.

BACKGROUND OF THE INVENTION

Certain polymers, copolymers and blends demonstrate piezoelectric behavior due to dipolar ferroelectricity residing in specific crystal phases. The most common of the semicrystalline ferroelectric polymers are poly(vinylidene fluoride) (PVDF) and its copolymer with trifluoroethylene, P(VDF-TrFE). As with any piezoelectrically active material, if electrodes are deposited on both of the major surfaces of a sample of piezoelectric film, the element functions as an electromechanical transducer and thus can be used as a sensor or actuator. If the film, operating as a sensor, is subjected to stress either in the direction corresponding to the film thickness, or in either of the transverse directions, an electric potential proportional to the applied stress is developed across the thickness of the film. The electrodes enable connection to external electronic circuitry, making it possible to process the information provided by the sensor.

Sensors having piezoelectric film transducers for passive detection of body sounds are known. See, e.g., U.S. Pat. Nos. 5,365,937 and 5,595,188 and published applications WO/92-08407 and WO/90-08506. However, known sensors may be characterized by undesirable performance constraints, including low signal to noise ratio, cross-talk, and signal contamination from power line harmonics or ambient room noise. These constraints may in part be attributable to transducer non-conformity to human body surfaces.

An improved thin-film sensor for the efficient passive detection of heart and blood-flow sounds is needed.

SUMMARY OF THE INVENTION

Integral components of the flexible thin-film sensor of this invention may comprise a piezoelectric film which may have a rectangular active area, a housing including film support means onto which the film is mounted, and a foot. The foot is the only sensor component intended to contact the skin. Hereafter these components are referred to as the "film", "housing", and "foot".

The invention may include sensors in which an initially slack piezoelectric film having fixed opposite edges is tented by the sensor mass to produce a stress upon vertical displacement of the acoustic medium, e.g., human flesh, upon which the sensor may be positioned.

The invention may also include sensors wherein the piezoelectric film is tensioned initially.

An important feature of the invention comprises sensors wherein the sensor spring constant is of the same order of magnitude and preferably matched to the spring constant of human flesh. It is preferred that the sensor be configured such that the film segment operates with a spring constant of from about 2 kN/m to about 4 kN/m.

The invention may comprise a single sensor or a plurality of individual sensors. A plurality of individual sensors may be assembled in a linear array or snake. A linear array may also comprise a plurality of links, each comprised of two or more individual sensors. Linear arrays of sensors may be positioned within a patient intercostal space (ICS). Undesired movement of a positioned array may be avoided by a laterally adjacent strip or laterally adjacent strips of adhesive tape.

A plurality of linear sensor arrays or of individual sensors may be positioned to accommodate a patient acoustic window.

DETAILED DESCRIPTION OF THE INVENTION

Figure 1:
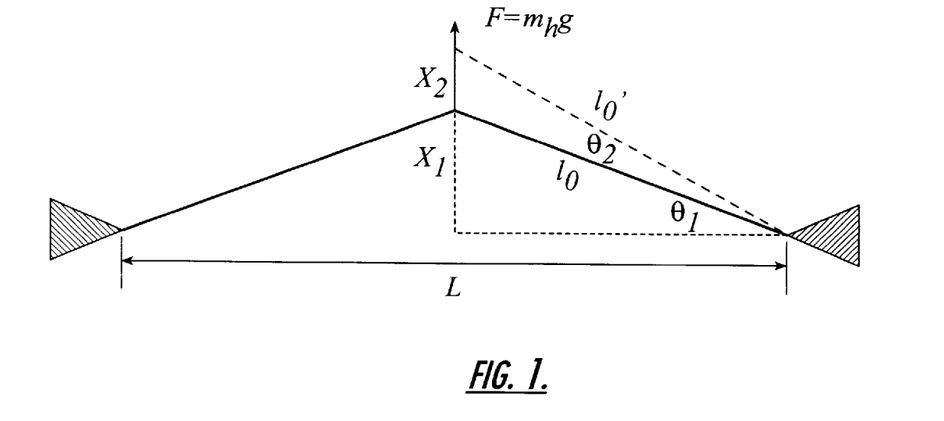
FIG. 1 is a schematic of a tented film (foot and housing not shown).
Figure 2:
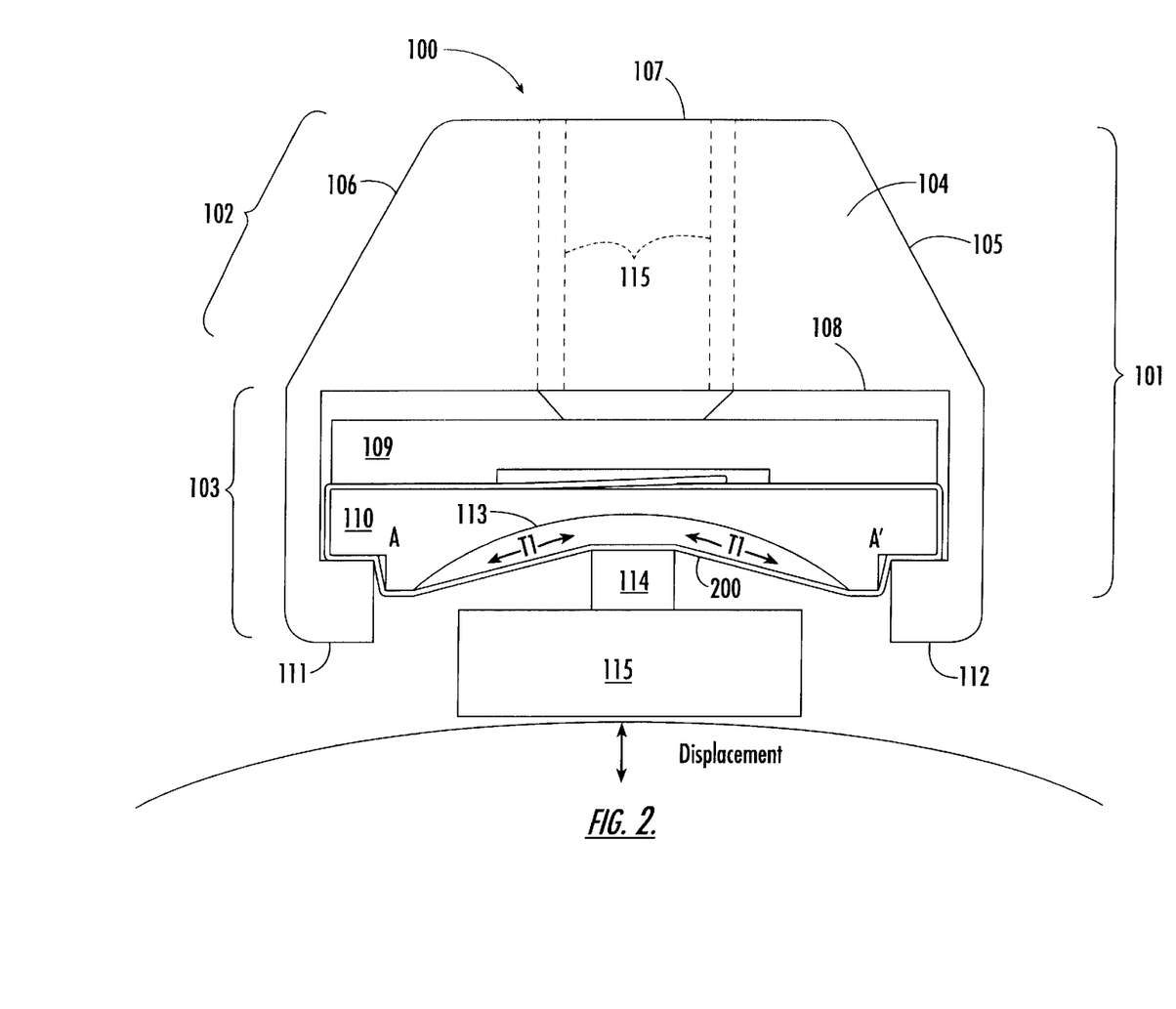
FIG. 2 is a section of a single sensor which may be in a link comprising a plurality of sensors. Links typically comprise three sensors. The housing, the upper and lower components of the film support structure within the housing, an arch in the lower film support component to accommodate a tented film, rails at the outer bottom edges of the housing and details illustrating the clamping of the film by the support structure are shown.
Figure 3:
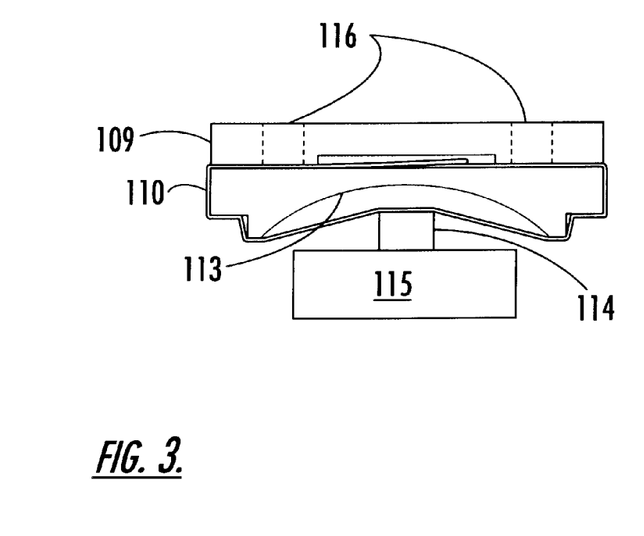
FIG. 3 is an assembly drawing. On the left, the film (with attached foot) and the two piece film support structure are shown disassembled. On the right the same components are shown assembled.

One preferred embodiment of the sensor is shown by FIGS. 1 to 3. The film is slightly longer than the distance between the points at which the film is fixed to the housing, so that the film is initially slack. Thus, when the sensor foot is put in contact with the surface of the intervening acoustic medium, the film is tented by the weight of the housing. For a given acoustic medium, e.g., a patient's chest, the sensitivity and frequency response of the sensor are dependent upon the housing mass, the surface area of the bottom of the foot, and the degree to which the film is tented (i.e., the "offset angle" θ). Referring to FIG. 1, if the foot is displaced vertically (i.e., the direction perpendicular to the upper surface of the sensor housing) just until the film is relieved of its slack, then the difference in vertical position between the resultant apex and a point at either of the fixed edges of the film is referred to as the "initial static displacement" ($X_1$ in the figure). The term "static" is used to differentiate the gross film displacement described here from the small transient displacements the device is designed to detect. When the sensor is placed in contact with the surface of the acoustic medium, the film is stretched by the load of the housing mass, providing an additional incremental static displacement ($X_2$). The sum of the initial and incremental static displacements comprise the total static displacement ($X_1+X_2$), which, for a given distance (L) determines the static offset angle ($\theta=\theta_1+\theta_2$) of the film.

It is apparent from FIG. 2 that a small transient displacement of the surface of the acoustic medium trapped beneath the sensor foot results in a corresponding vertical displacement of the foot, which produces a stress, $T_1$, along the length of the film. Since the film is piezoelectric, a voltage, v, proportional to the induced stress is generated between the film electrodes according to Equation 1

$$v = \frac{-d_{31}}{\varepsilon} T_1 t \quad (1)$$

where $d_{31}$ and $\varepsilon$ are the appropriate piezoelectric stress constant and dielectric permittivity of the film, respectively, and t is the film thickness.

The relative stiffness, $K_{eff}$, (reciprocal of compliance) of the tented film element and that for the acoustic medium, $K_{med}$, as seen by the sensor foot are important to the operation of the sensor. Specifically, broadband sensitivity is maximized for given housing mass and film dimensions when $K_{eff}=K_{med}$. For a film element of given dimensions, two parameters may be manipulated in order to match $K_{eff}=K_{med}$; total static displacement and sensor foot radius, respectively. Addressing the former, under sufficient mass loading, the film behaves like a nonlinear spring, for which the stiffness increases with increasing static displacement according to Equation 2:

$$K_{eff} = 4K\left(1 - \frac{L_O}{\sqrt{L^2+4X^2}}\right) + \frac{16KX^2 L_O}{(L^2+4X^2)^{\frac{3}{2}}}, \quad (2)$$

where $L_o$ is the length of the film, X is the total static displacement, L is the distance between housing rails, and K is the stiffness of the film given by Equation 3:

$$K = \frac{YA}{L_O}. \quad (3)$$

In Equation 3, Y is Young's modulus for the piezoelectric polymer, and A is the cross-sectional area through the width of the film. It should be noted that for practical housing mass the dominant component of X is the initial static displacement due to the slack in the film. With regard to the foot size, the apparent stiffness of the acoustic medium, as seen by the sensor, increases with increasing foot radius, a, according to Equation 4:

$$K_{med} = 6\pi a(\mu_1 - a\omega G'\sqrt{\rho/2}), \quad (4)$$

where $\rho$ is the density of the medium, and $\mu_1$ and $\mu_2$ are its Lamé constants, where $G'=\sqrt{|G|-\mu_1}$, where $G=\mu_1+j\omega\mu_2$ is the shear modulus of the medium. Thus the flesh beneath the sensor foot looks stiffer for a foot which contacts the skin over a larger area.

Figure 5:
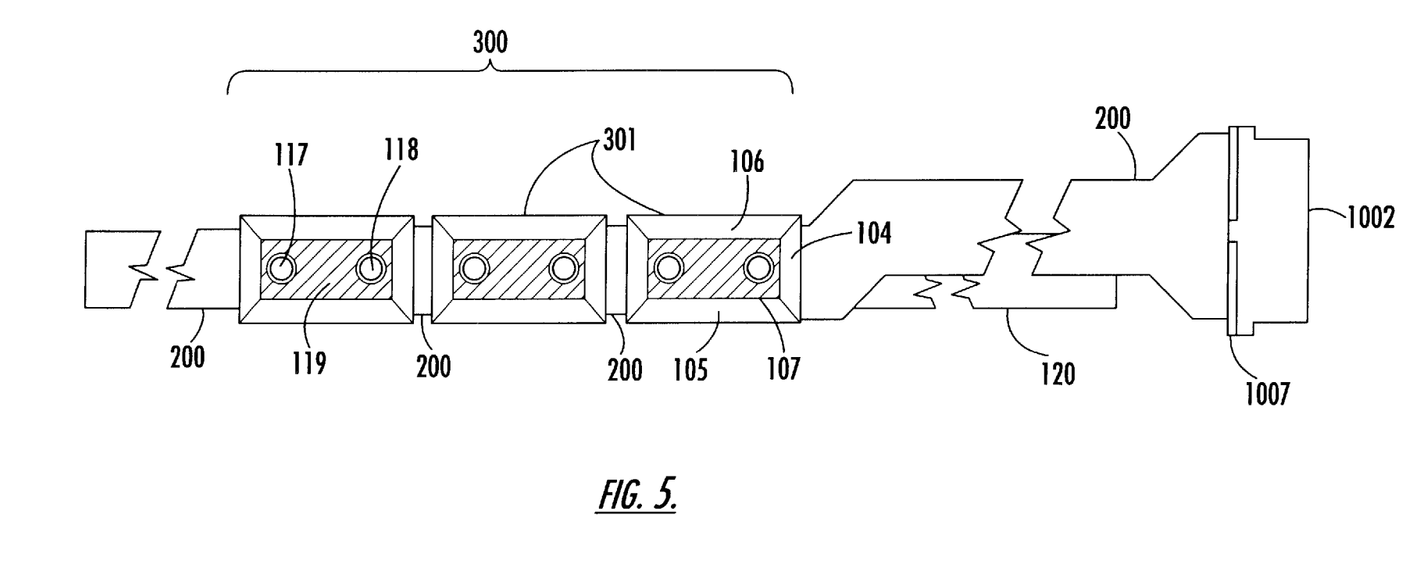
FIG. 5 is a top view of a single linear array or snake comprising three links, each comprising three sensors (nine sensors). Each of the three links may comprise one of the sensing areas of a film strip as shown by FIG. 4. A tape is shown adjacent each side of the three link array to eliminate undesirable sensor housing motion that may lead to mechanical cross-talk and to accommodate appropriate PVDF film tenting on a curved chest. Linear arrays comprising any desired number of links and sensors may be assembled in like manner.

As mentioned previously, the housing mass has a significant effect on the performance of the sensor. First, assuming all components of the sensor are allowed to move only in the vertical direction (the purpose of the tape of FIG. 5 is to reduce unwanted housing motion in the transverse directions), the response of the sensor to displacement of the surface with which it is in contact can be described as an under-damped, second-order, high-pass filter. The resonance frequency, $f_n$, of the filter is a function of the housing mass, $m_h$, the number of sensors in a single link, $n_s$, and the equivalent stiffness, $K_{eq}$ (the series combination of $K_{eff}$ and $K_{med}$ for a single sensor). The relationship is $$f_n = \sqrt{\frac{K_{eq}}{m_h/n_s}} \quad (5)$$

In Equation 5 the mass of the sensor foot and the entrained mass of the acoustic medium trapped beneath the foot are neglected since they are each much smaller than the housing mass. Secondly, the broadband sensitivity of the device increases with increasing housing mass, but practical considerations impose an upper limit on this parameter. These considerations include limits on patient tolerance of mass on his or her cheat and the threat of severely degrading sensor performance by having the housing rails come in contact with the patient's skin.

FIGS. 2 and 3 illustrate the design of a single, slack film, sensor having an initial static displacement angle $\theta_1$ of about 9°, a single sensor (link) housing mass of about 42 grams, and a spring constant of about 3 kN/m.

FIG. 2 shows a section of a single link 100 within a preferably metal housing 101 for a link of three sensors. The link housing comprises integral top and bottom parts 102, 103. The perimeter of housing part 102 is defined by a generally trapezoidal end wall 104, by sidewalls 105, 106, top 107 and bottom 108. Because the area of the top 107 is smaller than the area of the bottom 108, the end and sidewalls 104, 105 and 106 slope inwardly to render the top part 102 of the link housing trapezoidal in cross-section and so impart flexibility to a linear sensor array (see FIGS. 5 and 6). The bottom housing part 103 defines a chamber in which top and bottom film support components 109 and 110 are positioned. The outer bottom edges of the bottom housing part 103 provide sensor side rails 111 and 112.

A film 200 is shown pinched at the spaced apart points A, A' between the top and bottom film support components 109, 110. The film segment which spans the space between the pinch points is slack. An arch 113 in the lower film support element 110 accommodates tenting of the slack film 200.

The sensitivity of the sensors may increase as a function of the housing mass (film mass loading). In the preferred practice of the invention, the mass of a single housing is from about 40 grams to about 45 grams. However, the housing mass may be less, e.g., 20 grams, or greater, e.g., 200 grams.

Means 114, preferably plastic bars, attach circular foot 115 to the exposed lower surface of the film 200. In preferred embodiments of the invention, the circular foot has a diameter of 0.2 to 0.5 inch, preferably 0.3 to 0.4 inch. A polygonal foot of like area may be used instead of a circular foot. This foot and the support bars may be fabricated from any desired plastic, e.g., polystyrene, polypropylene, polycarbonate or the like.

The length of foot attachment means 114 is dimensioned to avoid patient skin contact of the sensor rails 111, 112 provided by the bottom part 103 of the housing as shown in FIG. 2.

A through hole 115 for a set screw to maintain the housing 101 and film support parts 109, 110 in assembly is shown (hashed lines).

FIG. 3 shows a sensor disassembled (left portion). Upper and lower film support parts 109 and 110 are shown with pins 116 and pin receiving holes 116a (hatched lines). The upper film support component is held in contact with the bottom component by friction between the pins 116.

Figure 4:
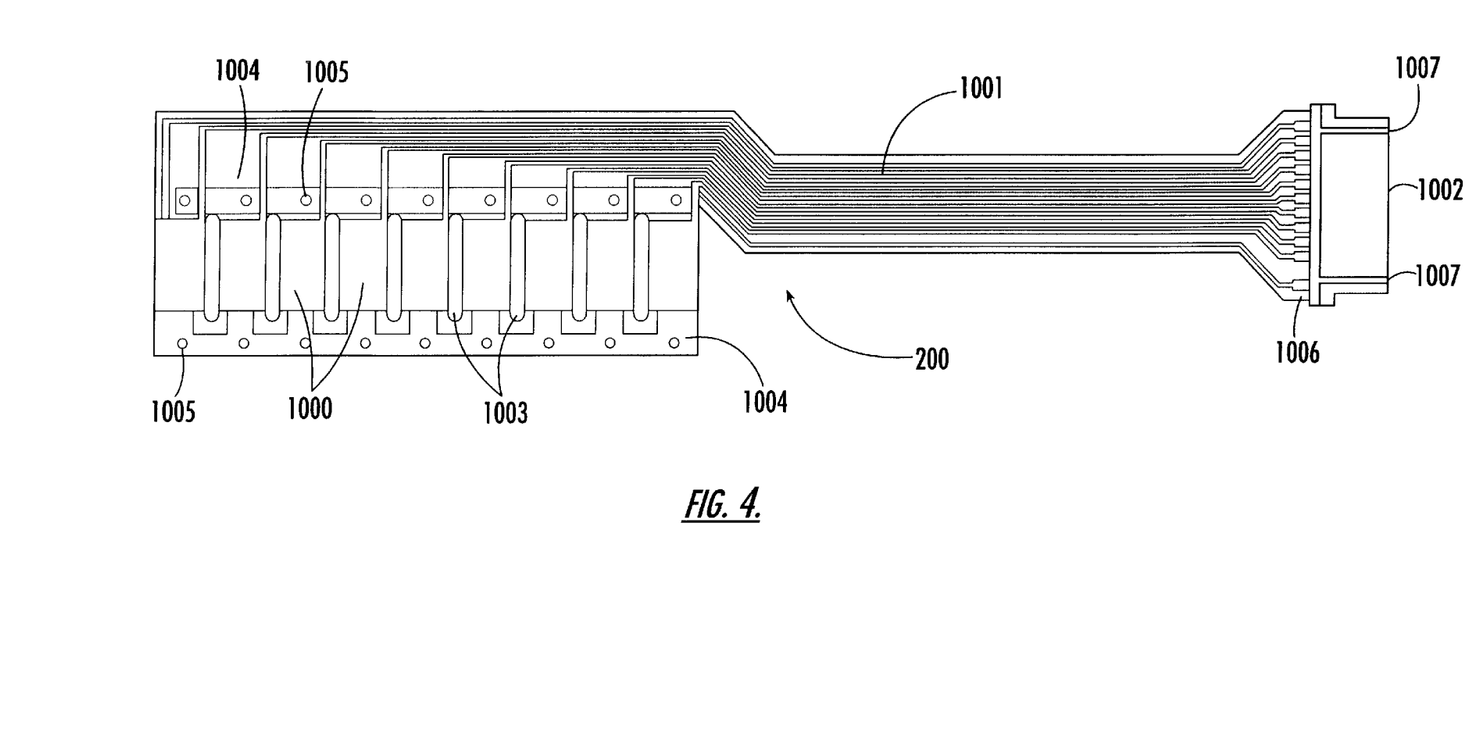
FIG. 4 depicts one side of a piezoelectric film strip. Nine conductive sensing areas, and details of the conductive ink printing on the film are shown. Because the film is transparent, some printing on the opposite side is illustrated as well.

FIG. 4 shows one side of a film 200 having nine rectangular spaced apart conductive sensing areas 1000 and associated printed conductive ink lines 1001 which connect the sensing areas to pins within a male component 1002 of a plastic connector. The sensing areas 1000 are equally spaced apart and separated by holes 1003 in the film 200. Stiffeners 1004 have holes 1005 for assembly pins (not shown). Connector 1002 houses conducting pins 1006. Polarity ridges 1007 are provided on the connector 1002 to facilitate proper orientation between the male 1002 and female (not shown) components of the connector.

The invention includes a linear array of sensors positioned on a continuous piezoelectric film strip having a plurality of separate sensing elements spaced longitudinally apart on a surface thereof. A plurality of similarly longitudinally spaced sensors is positioned along the strip, wherein each of said sensors comprises at least one of the plurality of sensing elements on the surface of film strip.

FIGS. 5 to 8 illustrate one embodiment of such a three-link (nine sensor) linear array 300 of links 301. Each link comprises three sensors 100 (not shown).

As shown in FIG. 5, the top of each link 301 has two holes 117 and 118 for set screws or like means to secure the link housing 101 to the film support components 109, 110 (see FIG. 2). A rectangular reflective tape piece 119 is affixed to the top of each sensor 100 to accommodate photogrammetric sensor location procedures.

Means for securing the three link linear sensor array against unwanted movement may be provided by adhesive tape 120 positioned at each side of the array.

As FIG. 5 shows, the portions of the film strip between each of the links included in the link 301 functions as a hinge to impart array flexibility to the array 300.

Housings are preferably metal. Zinc castings are appropriate to provide weight and shielding from electromagnetic interference.

Figure 6:
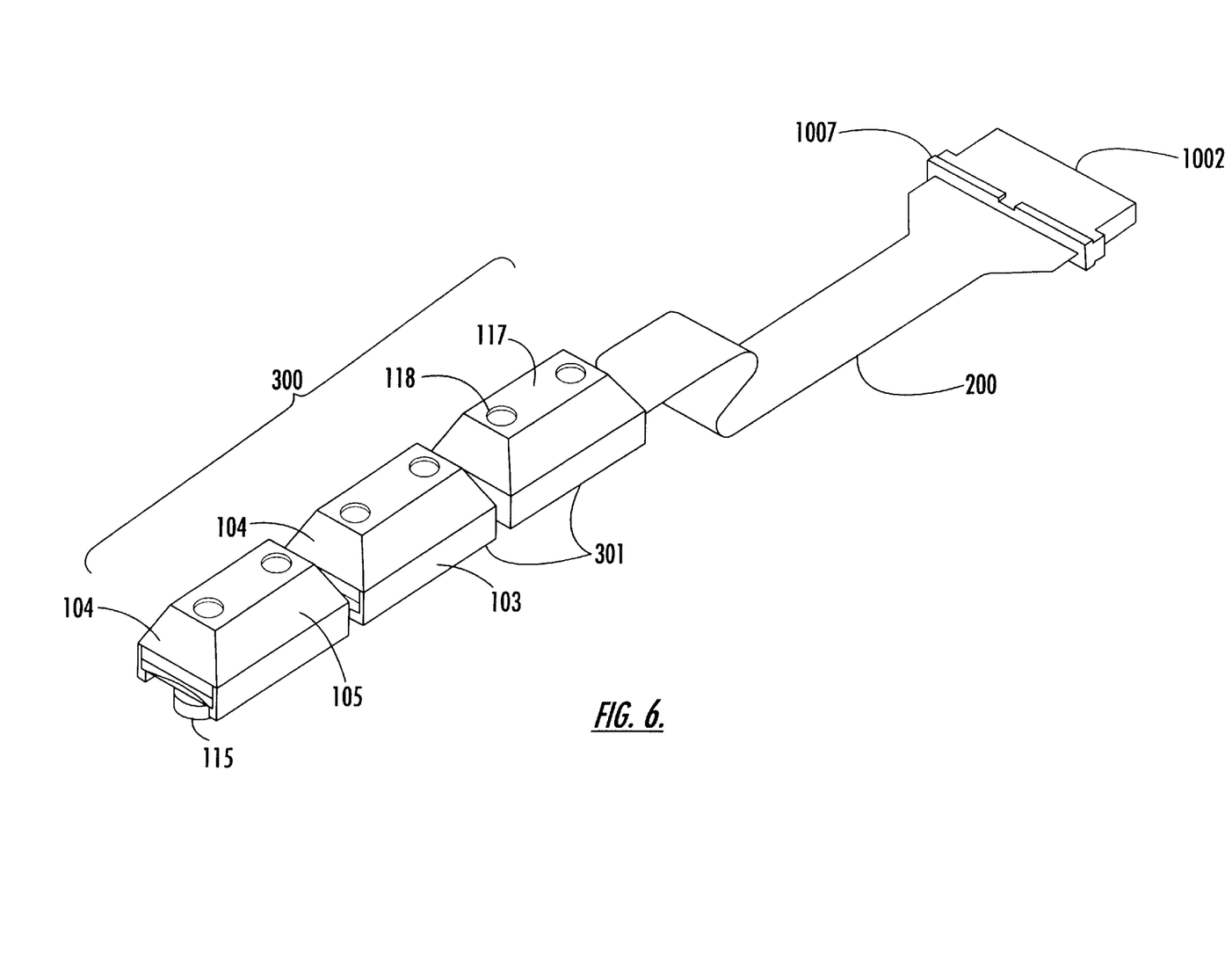
FIG. 6 illustrates a three dimensional view without the tape of a linear three link (nine sensor) array as shown by FIG. 5.
Figure 7:
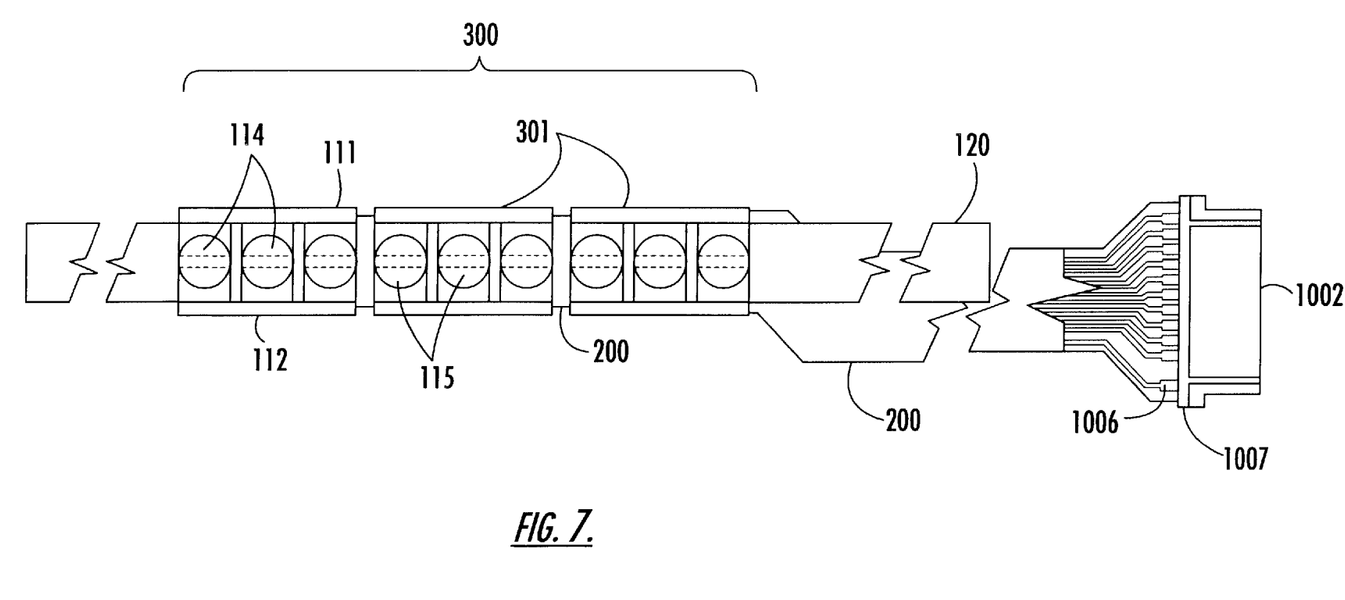
FIG. 7 is a bottom view of the snake of FIGS. 5 and 6 showing circular feet attached to the film with plastic bars (hashed lines) rectangular in cross-section. The feet may be other than circular, e.g., polygonal and the attachment means may be other than bars, e.g., discs.
Figure 8:
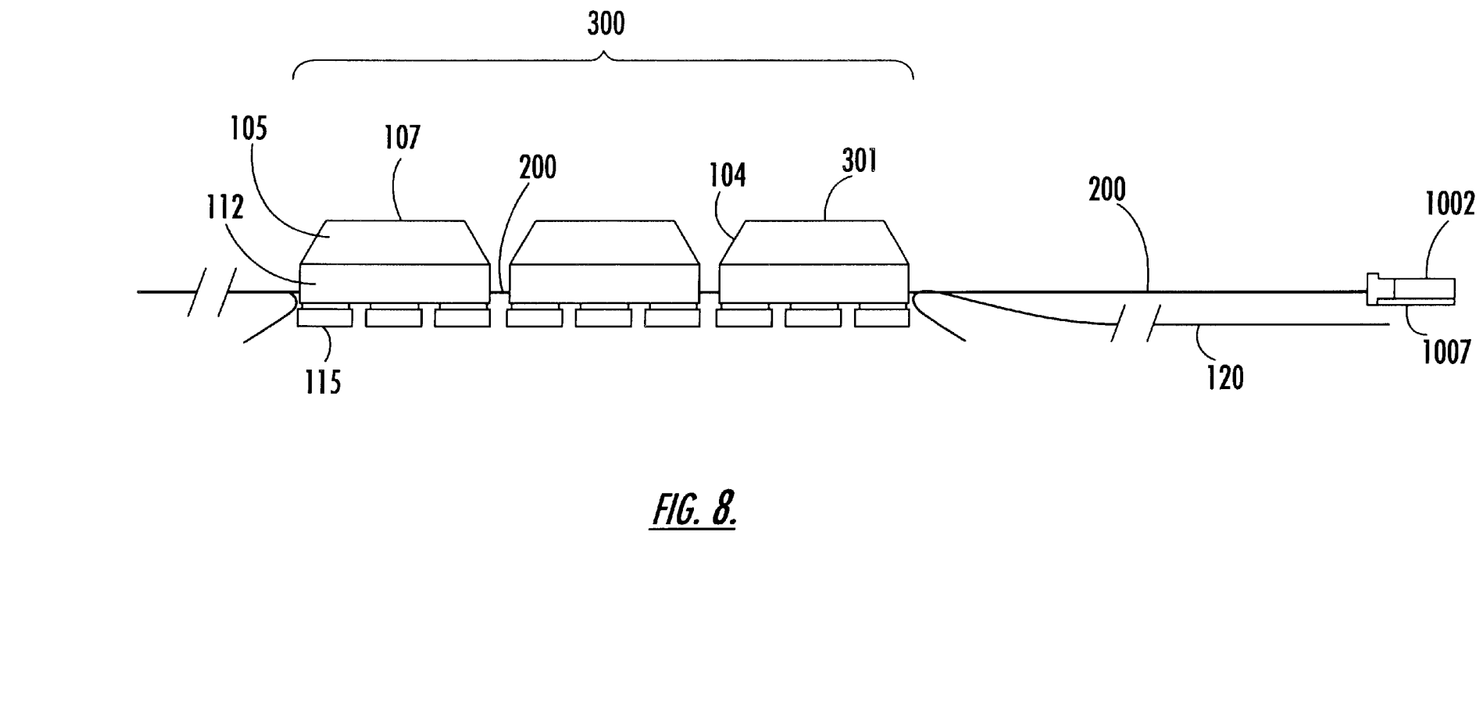
FIG. 8 is a side view of the three link (nine sensor) snake shown by FIGS. 5 and 6.
Figure 9:
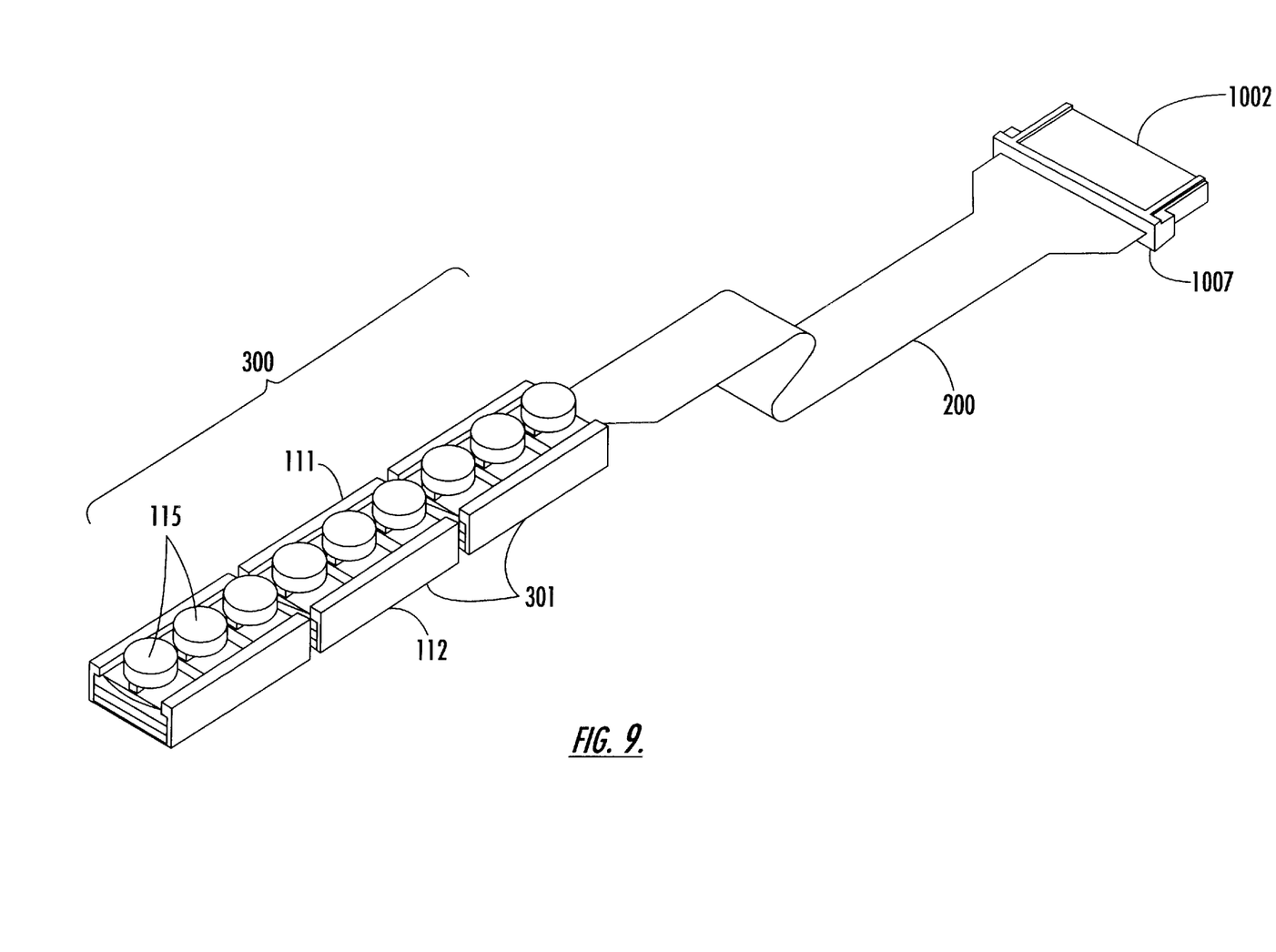
FIG. 9 is a three dimensional view of the underside of a three link (nine sensor) snake as shown by FIGS. 5 and 6.
Figure 10:
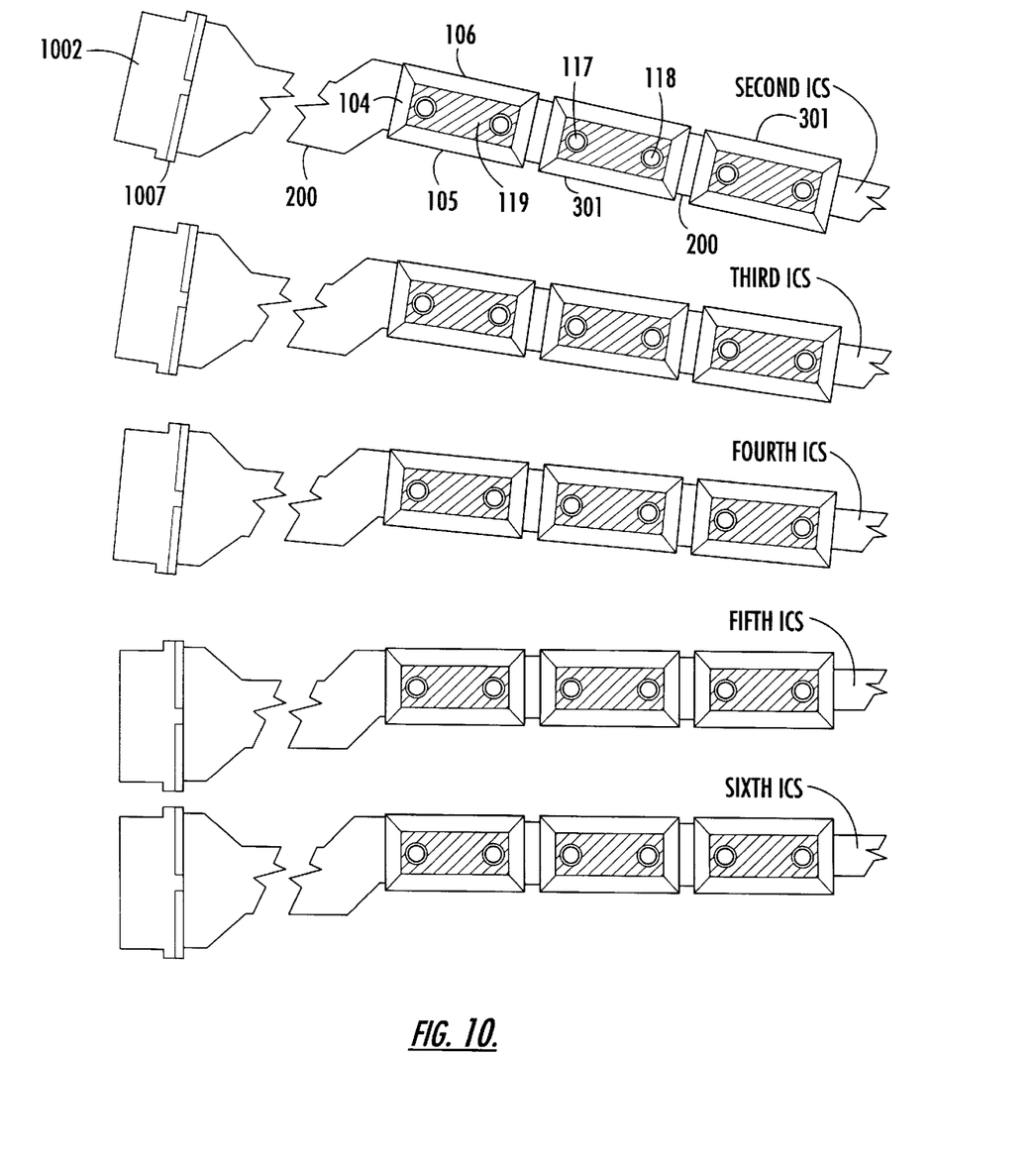
FIG. 10 illustrates five, three link snakes positioned one within each of the five intercostal spaces (ICS's) of a patient. The snakes are positioned to accommodate a patient acoustic window.

In a flexible linear array 300 as illustrated by FIGS. 5 and 6, individual links 300 are appropriately spaced apart (center to center).

Each flexible linear array is preferably capable of at least 10 degrees torsional rotation link-to-link from flat (by weight of the sensors alone) and a vertical hinge angle of at least +45 degrees and −30 degrees relative to the adjacent link. The spacing between each of the linear arrays included in a group or assembly of linear arrays may be as little as 2 cm or as wide as 4 cm (center-to-center). The back of each linear array is preferably flat to accommodate visual imaging. Links and sensor elements preferably do not rub or clang on each other in order that mechanical cross-talk is reduced.

Sensors included in an assembly or array preferably have interchannel phase differences of less than 1 degree standard deviation over the 100 Hz to 2 kHz frequency band when applied over the angles given. The sensor housing is preferably metal, e.g. zinc castings to provide weight and stability.

Sensor temperatures during data acquisition may lie between 20° C. and 38° C. Sensor-to-sensor variations may be as high as 10° C. External temperature differences and dynamics between array elements preferably do not affect interchannel phase specifications within the performance band between 100 Hz and 2 kHz.

The amplifier impedance to which each sensor may be attached (excluding cabling) is typically at 199 megohms in parallel with 25 pf or more.

Cross-talk between any two sensors, other than through the intended propagation path is preferably less than −30 dB.

Conventional individual sensor connectors and cabling are preferably mated with the array connector. Connector/cable design is selected to minimize external noise propagation down the cable into the sensors, and preferably adapt to the array layout on human contours so that array performance is not compromised.

We claim:

1. A sensor for the detection of sounds in an acoustic medium comprising:

(i) a generally laterally extending piezoelectric film segment having opposing first and second film edge portions and a central film portion located therebetween, wherein in position on a subject, said film segment configuration includes first and second inclined portions separated by said center portion and extending between a respective one of said first and second film edge portions and said center portion, wherein said first and second inclined portions vertically rise a distance from a respective one of said first and second edge portions to terminate into said center portion such that said center portion is located above said first and second film edge portions;

(ii) a foot adapted to reside on an acoustic body, wherein said foot is attached to said film segment center portion; and (iii) a housing having a mass associated therewith, first and second downwardly extending sidewalls and a central recess formed therebetween, said housing configured to hold said piezoelectric film segment therein such that said first and second film edge portions are securely held in position and said center portion is free to translate, vertically, wherein said mass of said housing causes tenting of said center portion of said film segment when said foot is placed in surface contact with said acoustic body, and wherein, during operation, said foot member extends downwardly outward from the bottom of said housing about said central recess, such that a lower portion of said foot member resides on the acoustic body below the bottom of said housing, and said foot member is able to translate vertically through said central recess to alter the tension on said film segment.

2. A sensor according to claim 1, wherein (i) the mass of said housing is from about 40 to about 50 grams; and (ii) said foot is circular and has a diameter of from about 0.2 to 0.5 inch.

3. A sensor according to claim 2, wherein said film is PVDF.

4. A sensor according to claim 1, wherein said film segment has a spring constant associated therewith of from about 2 kN/m to about 4 kN/m.

5. The sensor of claim 1, wherein the subject has an acoustic window associated therewith, and wherein said foot includes opposing upper and lower surfaces, said lower surface adapted to reside on the skin of the subject proximate to the subject's acoustic window and said upper surface is attached to said film segment center portion, and wherein said lower surface has a first cross-sectional area associated therewith and said upper surface has a second cross-sectional area associated therewith such that said first area is greater than said second area.

6. The sensor of claim 1, further comprising an attachment member positioned intermediate said foot and said film segment.

7. The sensor of claim 6, further comprising upper and lower film support components, said lower film support component includes a centrally located recess therein, and wherein said housing is configured with first and second opposing downwardly extending sidewalls and a central recess formed therebetween, said housing recess is sized and configured to receive said upper and lower film support components in overlying alignment therein, and wherein said first and second downwardly extending sidewalls are configured with lower siderails which laterally project toward the other opposing siderail to define an opening formed in the bottom of said housing to allow said foot member to extend therethrough and to provide a ledge upon which said film segment and said lower film support component cooperate to introduce localized holding forces onto said first and second film segment end portions.

8. The sensor of claim 6, wherein said housing has first and second opposing downwardly extending sidewalls and a center recess formed therebetween and wherein said housing center recess is configured to generally laterally extend a first width between said first and second downwardly extending sidewalls to define an opening formed in the bottom of said housing to allow said foot member to extend therethrough, and said foot is sized and configured to laterally extend a second width which is less than said first width.

9. The sensor of claim 8, wherein said attachment member has a width which is less than a minor portion of said second width, and wherein said attachment member extends a distance into said housing central recess.

10. The sensor of claim 1, wherein said housing has an upper body portion which in cross section has a generally trapezoidal configuration.

11. A sensor for the acoustic detection of heart or blood flow sounds, comprising:
(i) a housing having a mass associated therewith and first and second opposing downwardly extending sidewalls and a central recess formed therebetween;
(ii) a piezoelectric film segment having opposing first and second end portions and a center portion therebetween, said first end portion affixed to a lower portion of said first downwardly extending sidewall and said second end portion affixed to a lower portion of said second downwardly extending sidewall, said film segment positioned in said housing such that said center portion is aligned with said housing central recess; and
(iii) a foot member attached to said center portion of said piezoelectric film segment, said foot member adapted to reside on the chest of a subject,
wherein, in position, a lower portion of said foot member rests on the subject below a lowest portion of said housing and said housing sidewalls are located above the subject such that said housing mass is suspended above the subject supported by said film segment about said foot member and said film segment center portion resides at a vertical distance above said first and second film segment end portions and said first and second film segment end portions are affixed to said housing in a manner which introduces tension onto said film segment, whereby, in operation, translation of said film center portion responsive to displacement of said foot member varies the tension in said film segment.

12. A sensor configured for positioning on an external surface of a subject for the acoustic detection of heart or blood flow sounds, comprising:
(i) a housing having a mass associated therewith and first and second opposing downwardly extending sidewalls and a central recess formed therebetween and with an aperture extending through a bottom portion of said housing;
(ii) a generally laterally extending piezoelectric film segment having first and second major surfaces, and opposing first and second end portions and a center portion therebetween, each of said first and second end portions held in position by contact with a respective one of said first and second downwardly extending sidewalls such that said film center portion resides in said housing center recess, wherein said first major surface is oriented to face the inside of said housing and said second major surface is oriented to face the subject; and
(iii) a foot adapted for contact with the external surface of the subject, wherein a lower portion of said foot extends below a lowest portion of said housing through said aperture, and wherein said foot is arranged in said housing such that, in operation, said foot is able to vertically translate through said aperture unrestricted by the bottom of said housing,
wherein said foot is attached to said second major surface proximate said center portion of said film segment.

13. A sensor according to claim 12, further comprising an internal housing bridging member with a recessed portion configured to hold said film segment substantially thereagainst while allowing said central portion of said film segment translate about said recessed portion, wherein said first and second downwardly extending sidewalls are configured as housing outer walls, each having inner surface ledges which generally laterally extend toward the other, and wherein each side inner surface ledge is sized and configured to pinch a respective one of said film segment first and second end portions against said internal bridging member to define first and second pinching points.

14. A sensor according to claim 12, further comprising an attachment member positioned intermediate said foot and said film segment such that said foot is indirectly attached to said second major surface of said film segment, and wherein said foot and said attachment member each has a vertical length which is sufficient to inhibit said downwardly extending sidewalls from contacting the patient in position thereon.

15. A sensor according to claim 12, wherein said piezoelectric film segment has a spring constant which is of the same order of magnitude as the nominal spring constant of human flesh.

16. A sensor according to claim 12, wherein said piezoelectric film segment has a spring constant associated therewith which is from about 2 kN/m to about 4 kN/m.

17. The sensor of claim 12, wherein the subject has an acoustic window associated therewith, and wherein said foot includes opposing upper and lower surfaces, said lower surface adapted to reside on the skin of the subject proximate to the subject's acoustic window and said upper surface is attached to said film segment center portion, and wherein said lower surface has a first cross-sectional area associated therewith and said upper surface has a second cross-sectional area associated therewith such that said first area is greater than said second area.

18. The sensor of claim 12, further comprising an attachment member positioned intermediate said foot and said film segment.

19. The sensor of claim 18, further comprising upper and lower film support components, wherein said housing recess is sized and configured to receive overlying upper and lower film support components therein, said lower film support component including a centrally located arcuate recess therein, and wherein said first and second downwardly extending sidewalls are configured with lower siderails which laterally project toward the other opposing side rail and define said aperture in the bottom of said housing and to provide a ledge upon which said film abuts to cooperate with lower portions of said lower film support component to introduce localized pinching forces onto said first and second film segment end portions.

20. The sensor of claim 18, wherein said aperture in the bottom of said housing is configured to generally laterally extend a first width between said first and second downwardly extending sidewalls and said foot is sized and configured to laterally extend a second width which is less than said first width.

21. The sensor of claim 20, wherein said attachment member has a width which is less than a minor portion of said second width.

22. The sensor of claim 12, wherein said housing has an upper body portion which in cross section has a generally trapezoidal configuration.

23. A device for the detection of the heart and blood flow sounds of a subject which comprises:
  (i) a housing having a mass associated therewith and first and second opposing downwardly extending sidewalls and a central recess region formed therebetween, wherein the bottom of said housing includes an opening formed therein;
  (ii) a plurality of piezoelectric sensors held within said housing, wherein said piezoelectric sensors each include a generally laterally extending piezoelectric film segment having first and second major surfaces, and opposing first and second end portions and a center portion therebetween, wherein said housing is sized and configured to hold each of said film segments spatially separated and substantially aligned therein, wherein each of said film segment center portions are positioned within said housing center recess such that they are individually free to translate thereabout, wherein said first major surface of each of said film segments is oriented to face the inside of said housing and said second major surface is oriented to face the subject; and
  (iii) a plurality of feet, wherein a respective one foot corresponds to each film segment, a lower portion of each foot extending below a lowest portion of said housing and being adapted to reside on the external surface of the subject and, wherein said feet are arranged in said housing such that, in operation, at least a portion of each foot is able to translate vertically through the bottom opening of said housing,
wherein a respective one of said feet is attached to a respective center portion of each of said second major surfaces of said film segments.

24. A device according to claim 23, wherein said plurality of piezoelectric sensors is at least three piezoelectric sensors.

25. A device according to claim 23, further comprising:
  an internally disposed housing bridging member with a recessed portion configured to hold said film segments substantially thereagainst while allowing said central portion of said film segments to translate about said bridging member recessed portion, wherein said first and second downwardly extending sidewalls are configured as housing outer walls, each having inner surface ledges which generally laterally extend toward the other, and wherein each sidewall inner surface ledge is sized and configured to pinch a respective one of said film segments first and second end portions against said internal bridging member to define first and second pinching points, and wherein, in operation said feet are arranged in said housing such that each of said feet are able to translate through said opening unrestricted by the bottom of the housing.

26. A device according to claim 23, further comprising a plurality of attachment members, a respective one positioned intermediate of each corresponding foot and film segment such that said feet are indirectly attached to said second major surface of said film segments, and wherein said feet and said attachment members define a vertical length which is sufficient to inhibit said downwardly extending sidewalls and said bottom of said housing from contacting the subject when in position thereon.

27. The device of claim 23, wherein the subject has an acoustic window associated therewith, and wherein said feet include opposing upper and lower surfaces, such that said lower surfaces are adapted to reside on the skin of the subject proximate to the subject's acoustic window and a respective one of said upper surfaces are attached to a respective one of said film segment center portions, and wherein said lower surfaces have a first area associated therewith and said upper surfaces have a second area associated therewith such that said first area is greater than said second area.

28. The device of claim 23, further comprising an attachment member positioned intermediate said foot and said film segment.

29. The device of claim 28, further comprising upper and lower film support components, wherein said housing recess is sized and configured to receive overlying upper and lower film support components therein, said lower film support component including a centrally located recess therein, and wherein said first and second downwardly extending sidewalls are configured with lower siderails which laterally project toward the other opposing side rail to define said opening in the bottom of said housing and provide a ledge upon which said film segments reside against such that said lower film support component and said film segments cooperate with said ledges to introduce localized pinching forces onto end portions of said first and second film segments.

30. The device of claim 28, wherein said opening in the bottom of said housing is configured to generally laterally extend a first width between said first and second downwardly extending sidewalls and said foot is sized and configured to laterally extend a second width which is less than said first width.

31. The device of claim 30, wherein said attachment member has a width which is less than a minor portion of said second width.

32. The device of claim 23, wherein said housing has an upper body portion which in cross section has a generally trapezoidal configuration.

33. The device of claim 23; wherein said first and second end portions are held in position by contact with a respective one of said first and second downwardly extending sidewalls.

* * * * *

UNITED STATES PATENT AND TRADEMARK OFFICE
CERTIFICATE OF CORRECTION

PATENT NO. : 6,261,237 B1
DATED : July 17, 2001
INVENTOR(S) : Swanson et al.

Page 1 of 1

It is certified that error appears in the above-identified patent and that said Letters Patent is hereby corrected as shown below:

<u>Title page,</u>
Item [56], OTHER PUBLICATIONS, the following should appear:

Nilsson et al., "A Combined Microphone for Simultaneous Recording of Pulse, Phono and Reference ECG," *Electromedica*, Vol. 2, No. 76, pp. 64-68 (1976).

Oestreicher, "Field and Impedance of an Oscillating Sphere in a Viscoelastic Medium with an Application to Biophysics," *J. Acoust. Soc. Am.*, Vol. 23, No. 6, pp. 707-714 (November 1951).

Verburg, "Transmission of Vibrations of the Heart to the Chestwall," *Adv. Cardiovasc. Phys.*, Vol. 5 (Part III), pp. 84-103 (1983).

Signed and Sealed this

Twelfth Day of March, 2002

*Attest:*

*Attesting Officer*

JAMES E. ROGAN
*Director of the United States Patent and Trademark Office*